United States Patent
Goel et al.

(10) Patent No.: US 9,808,299 B2
(45) Date of Patent: Nov. 7, 2017

(54) BIOACTIVE FUSION DEVICE

(71) Applicant: The University of Toledo, Toledo, OH (US)

(72) Inventors: Vijay K. Goel, Holland, OH (US); Anand K. Agarwal, Ottawa Hills, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/375,942

(22) PCT Filed: Jan. 31, 2013

(86) PCT No.: PCT/US2013/024033
§ 371 (c)(1),
(2) Date: Jul. 31, 2014

(87) PCT Pub. No.: WO2013/116452
PCT Pub. Date: Aug. 8, 2013

(65) Prior Publication Data
US 2014/0350608 A1 Nov. 27, 2014

Related U.S. Application Data

(60) Provisional application No. 61/593,270, filed on Jan. 31, 2012.

(51) Int. Cl.
*A61B 17/86* (2006.01)
*A61F 2/44* (2006.01)
(Continued)

(52) U.S. Cl.
CPC ........ *A61B 17/866* (2013.01); *A61B 17/7064* (2013.01); *A61B 17/8625* (2013.01);
(Continued)

(58) Field of Classification Search
CPC .............. A61B 17/866; A61B 17/7064; A61B 17/8685; A61B 17/8625; A61B 2017/564; A61F 2/442; A61F 2/4455; A61F 2/446
(Continued)

(56) References Cited

U.S. PATENT DOCUMENTS 6,537,274 B1 * 3/2003 Katz ...................... A61B 17/62
606/304
8,840,677 B2 * 9/2014 Kale .................... A61B 17/686
606/313

(Continued)

FOREIGN PATENT DOCUMENTS

EP 2206470 A2 7/2010
EP 2228015 A2 9/2010
(Continued)

OTHER PUBLICATIONS

PCT International Search Report and the Written Opinion, Application No. PCT/US2014/043830 filed Jun. 24, 2014, dated Nov. 14, 2014.
(Continued)

*Primary Examiner* — Pedro Philogene
*Assistant Examiner* — David C Comstock
(74) *Attorney, Agent, or Firm* — MacMillan, Sobanski & Todd, LLC

(57) ABSTRACT

In a first broad aspect, there is provided herein a bioactive device and system for fusion between two bones, two parts of a bony joint, or a bony defect, such as of the spine. The fusion device includes a screw having a head and a threaded shaft. The fusion device also includes a bone dowel having an internal bore of which at least a distal portion is threaded to engage the threads of the screw shaft. The bone dowel is made of a bone-like, biocompatible, or allograft material to provide a layer of bone-like, biocompatible, or allograft
(Continued)

material between the screw and the spinal bone. The device is generally coaxial and is further described in the drawings and description herein.

13 Claims, 12 Drawing Sheets

(51) Int. Cl.
    *A61B 17/70*     (2006.01)
    *A61B 17/56*     (2006.01)

(52) U.S. Cl.
    CPC .......... *A61B 17/8685* (2013.01); *A61F 2/442* (2013.01); *A61F 2/4455* (2013.01); *A61B 2017/564* (2013.01); *A61F 2/446* (2013.01)

(58) Field of Classification Search
    USPC ....... 606/247, 248, 249, 300, 301, 302, 304, 606/306, 309, 310, 313, 322; 623/17.11
    See application file for complete search history.

(56) References Cited

U.S. PATENT DOCUMENTS

| | | |
|---|---|---|
| 2004/0034427 A1 | 2/2004 | Goel et al. |
| 2007/0162132 A1* | 7/2007 | Messerli ................ A61B 17/68 623/17.11 |
| 2008/0288003 A1 | 11/2008 | McKinley |
| 2008/0300634 A1 | 12/2008 | Gray |
| 2009/0036926 A1 | 2/2009 | Hestad |
| 2010/0082071 A1 | 4/2010 | Moumene |
| 2011/0087294 A1 | 4/2011 | Reiley |
| 2011/0144766 A1 | 6/2011 | Kale et al. |
| 2011/0160772 A1 | 6/2011 | Arcenio et al. |
| 2011/0184478 A1 | 7/2011 | Reiley |
| 2011/0295319 A1 | 12/2011 | Duplessis et al. |
| 2011/0319946 A1 | 12/2011 | Levy et al. |
| 2012/0083883 A1 | 4/2012 | Ginn |
| 2012/0109222 A1 | 5/2012 | Goel et al. |

FOREIGN PATENT DOCUMENTS

| | | |
|---|---|---|
| WO | 2013018062 A1 | 2/2013 |
| WO | 2013052807 A2 | 4/2013 |
| WO | 2013116452 A2 | 8/2013 |
| WO | 2014209976 A2 | 12/2014 |

OTHER PUBLICATIONS

PCT International Search Report and the Written Opinion, Application No. PCT/US2013/024033 filed Jan. 31, 2013, dated May 13, 2013.

Chinese Notification of First Office Action, Application No. CN 201380013369.X, dated Feb. 1, 2016.

European Search Report, Application No. 13743220.9, dated Jan. 12, 2016.

Extended European Search Report, Application No. EP14817934.4, dated Jan. 25, 2017.

* cited by examiner

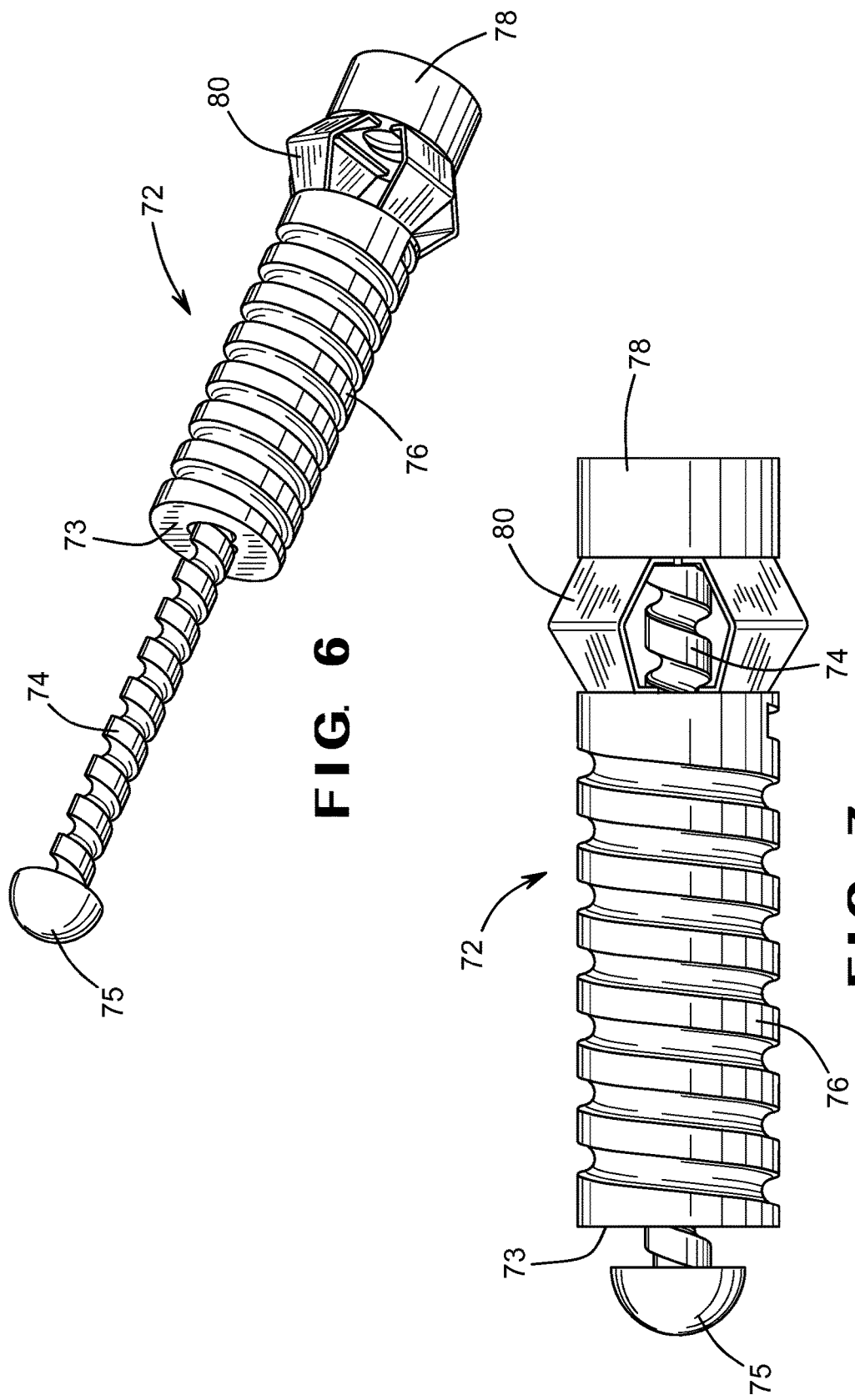

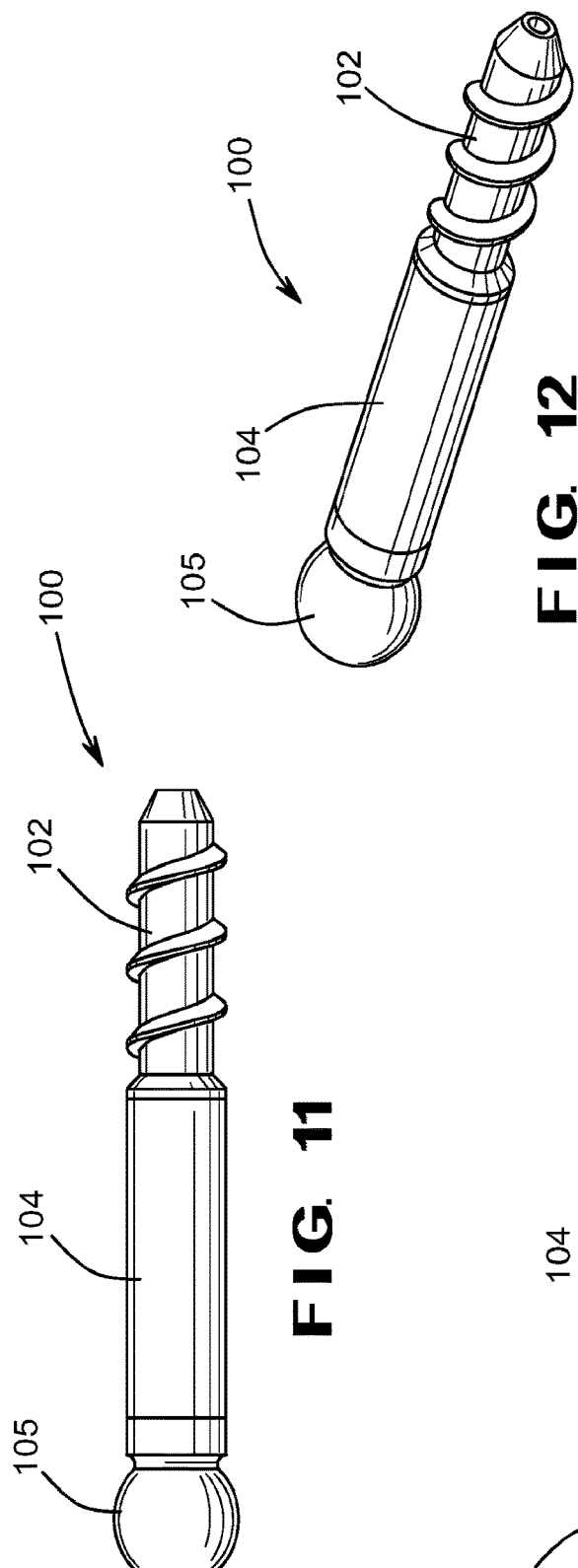
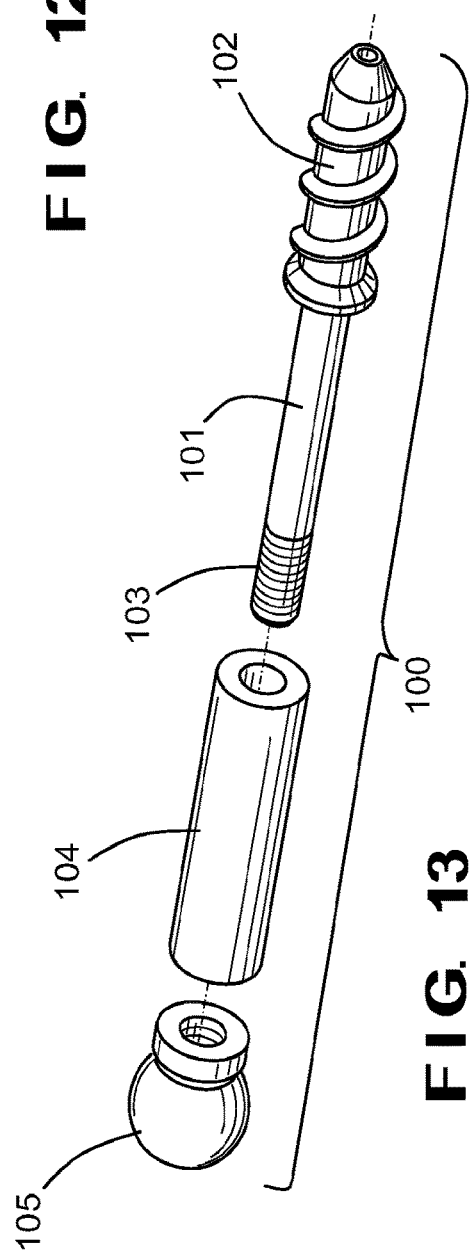
FIG. 11
FIG. 12
FIG. 13

BIOACTIVE FUSION DEVICE

CROSS-REFERENCE TO RELATED APPLICATIONS

This application claims the benefit of U.S. Provisional Application No. 61/593,270, filed Jan. 31, 2012, the disclosure of which is incorporated herein by reference.

STATEMENT REGARDING FEDERALLY SPONSORED RESEARCH

The invention was not made with government support, and the government has no rights in the invention.

TECHNICAL FIELD AND INDUSTRIAL APPLICABILITY

This invention relates, in part, to a bioactive system for fusion between two bones, two parts of a bony joint, or a bony defect, such as of the spine. This invention also relates, in part, to methods of making and methods of using such a bioactive system for fusion.

BACKGROUND OF THE INVENTION

Over 650,000 spine surgeries are performed annually in the United States, with the majority being decompressive laminectomies for spinal stenosis. Spinal stenosis is a narrowing of the spinal canal housing the spinal cord, which is generally caused by arthritis of articulating bones of the vertebral column and/or bulging of the intervertebral discs. Eighty percent of the population report having back pain, with over 400,000 patients per year diagnosed with spinal stenosis. The majority age group is 65 or older. The diagnosis of spinal stenosis and, therefore, need for treatment is likely to escalate rapidly when U.S. census data is applied. For example, the U.S. population of individuals over 65 represented 12.4% (about 35 million) in 2000 and is projected to represent 19.6% (million) by the year 2030.

The most common treatment for spinal stenosis involves a midline approach with a decompressive laminectomy to address the stenosis. Although highly effective in relieving the clauditory symptomotology, there is growing evidence and concern over the need for reoperation to address reoccurrence of symptoms related to progression of spondylolisthesis, or slippage, at the site of decompression. Slippage rates post-surgery have been reported as high as 20% in "no preop slip" patients and from 40% to 100% in "preop slip present" patients. The reoperation rate for each of these groups varies and is dependent on many factors. Reported reoperation rates average around 18% for the "no preop slip" group and upward of 30% for the "preop slip present" group.

The concern for further slippage and need for reoperation has fostered a treatment method involving the use of dynamic or motion sparing devices placed without a fusion to give some amount of "stiffness" to prevent further slippage and yet allow for some motion, avoid excessive loading of adjacent segments, and hopefully avoid adjacent segment disease. Such devices have been successful in limiting the progression of slip in stable spine constructs. However, there are recent reports of instrumentation failures and the need for revision surgery. Thus, the uses of dynamic systems are not always clinically successful and may defeat the attempt to limit reoperations. Furthermore, it is reported that adjacent segment disease continues similar to patients with rigid fusions. Furthermore, the need to utilize pedicle screw technology and approaches with such dynamic systems makes the muscle trauma morbidity comparable to undergoing a fusion surgery with screws and/or rods. Thus, alternative instrumentation is being explored by surgeons and engineers alike.

SUMMARY OF THE INVENTION

In a first broad aspect, there is provided herein a bioactive device and system for fusion between two bones, two parts of a bony joint, or a bony defect, such as of the spine. The fusion device includes a screw having a head and a threaded shaft. The fusion device also includes a bone dowel having an internal bore of which at least a distal portion is threaded to engage the threads of the screw shaft. The bone dowel is made of a bone-like, biocompatible, or allograft material to provide a layer of bone-like, biocompatible, or allograft material between the screw and the spinal bone. The device is generally coaxial and is further described in the drawings and description herein.

In another aspect, a method of fixation of two bones, two parts of a bony joint, or a bony defect, such as of the spine is disclosed. For example, a method of fixation of a facet joint of two vertebrae includes the step of inserting a fusion device through the inferior articular process of a first vertebra, transversely across a facet joint, and into the superior articular process of a second adjacent vertebra. The fusion device includes a screw having a head and a threaded shaft and a bone dowel having an internal bore, of which least a distal portion is threaded to engage the threads of the screw shaft. The bone dowel is made of a bone-like, biocompatible, or allograft material to provide a layer of the bone-like, biocompatible, or allograft material between the screw and the spinal bone. The screw is threaded into the bore of the dowel to secure the two vertebrae together across the facets.

An advantage of the fusion device is reduced medical costs from a less invasive surgical procedure. Another advantage is the reduced amount of slippage and re-operations that are required. A further advantage is the achievement of comparable stabilization of the spine with minimal invasiveness.

Various aspects of this invention will become apparent to those skilled in the art from the following detailed description of the preferred embodiment, when read in light of the accompanying drawings.

BRIEF DESCRIPTION OF THE DRAWINGS

The accompanying drawings, incorporated herein and forming a part of the specification, illustrate the present invention in its several aspects and, together with the description, serve to explain the principles of the invention. In the drawings, the thickness of the lines, layers, and regions may be exaggerated for clarity.

FIG. 6 is an enlarged perspective view of the second embodiment of the bone screw portion illustrated in FIG. 3 coaxially aligned with the bone dowel portion of the first embodiment of the fusion device.

FIG. 7 is an enlarged elevational view of the second embodiment of the bone screw portion illustrated in FIG. 3 partially threaded within the bone dowel portion of the first embodiment of the fusion device.

FIG. 11 is an elevational view of a second embodiment of a fusion device in accordance with this invention.

FIG. 12 is a perspective view of the second embodiment of a fusion device illustrated in FIG. 11.

FIG. 13 is an exploded perspective view of the second embodiment of a fusion device illustrated in FIGS. 11 and 12.

DETAILED DESCRIPTION OF THE EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including books, journal articles, published U.S. or foreign patent applications, issued U.S. or foreign patents, and any other references, are each incorporated by reference in their entireties, including all data, tables, figures, and text presented in the cited references.

Unless otherwise indicated, all numbers expressing ranges of magnitudes, such as quantities of ingredients, properties such as molecular weight, reaction conditions, dimensions, and so forth as used in the specification and claims are to be understood as being modified in all instances by the term "about." Any numerical values inherently contain certain errors necessarily resulting from error found in their respective measurements. Accordingly, unless otherwise indicated, the numerical properties set forth in the specification and claims are approximations that may vary depending on the desired properties sought to be obtained in embodiments of the present invention. All numerical ranges are understood to include all possible incremental subranges within the outer boundaries of the range. Thus, a range of 30 degrees to 90 degrees discloses, for example, 35 degrees to 50 degrees, 45 degrees to 85 degrees, and 40 degrees to 80 degrees, etc.

Figure 1A:
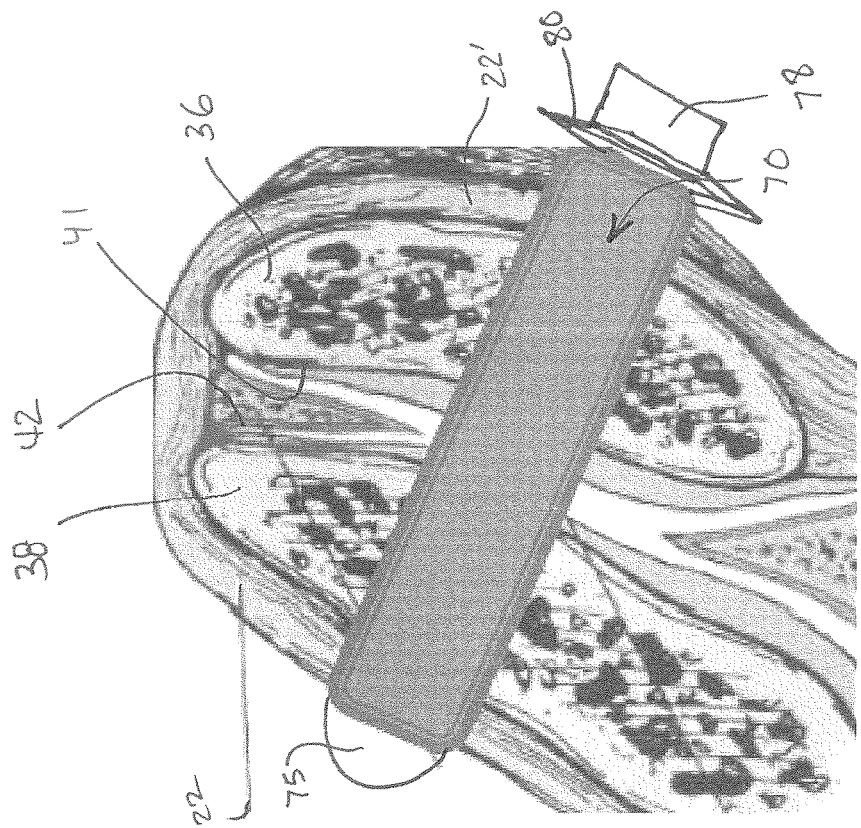
FIG. 1A is an enlarged view of portions of the two vertebrae illustrated in FIG. 1 and including a schematic representation of a fusion device fixing such vertebrae together in accordance with this apparatus and method of this invention.
Figure 1:
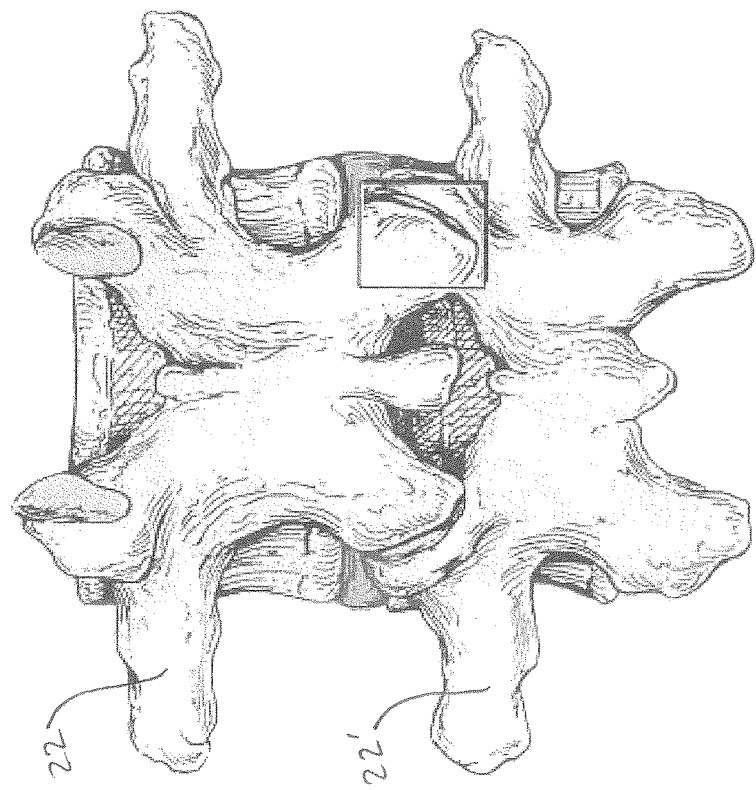
FIG. 1 is an elevational view showing two vertebrae in a portion of a human spine.

FIG. 1 is an elevational view showing two vertebrae 22 and 22', such as in a portion of a human spine. Although this invention will be described and illustrated in the context of a fusion of a facet joint between the two vertebrae 22 and 22', it will be appreciated that this invention may be practiced for any other purpose in any other environment. For example, this invention may be practiced to perform a fusion between two bones, two parts of a bony joint, or a bony defect.

Figure 1B:
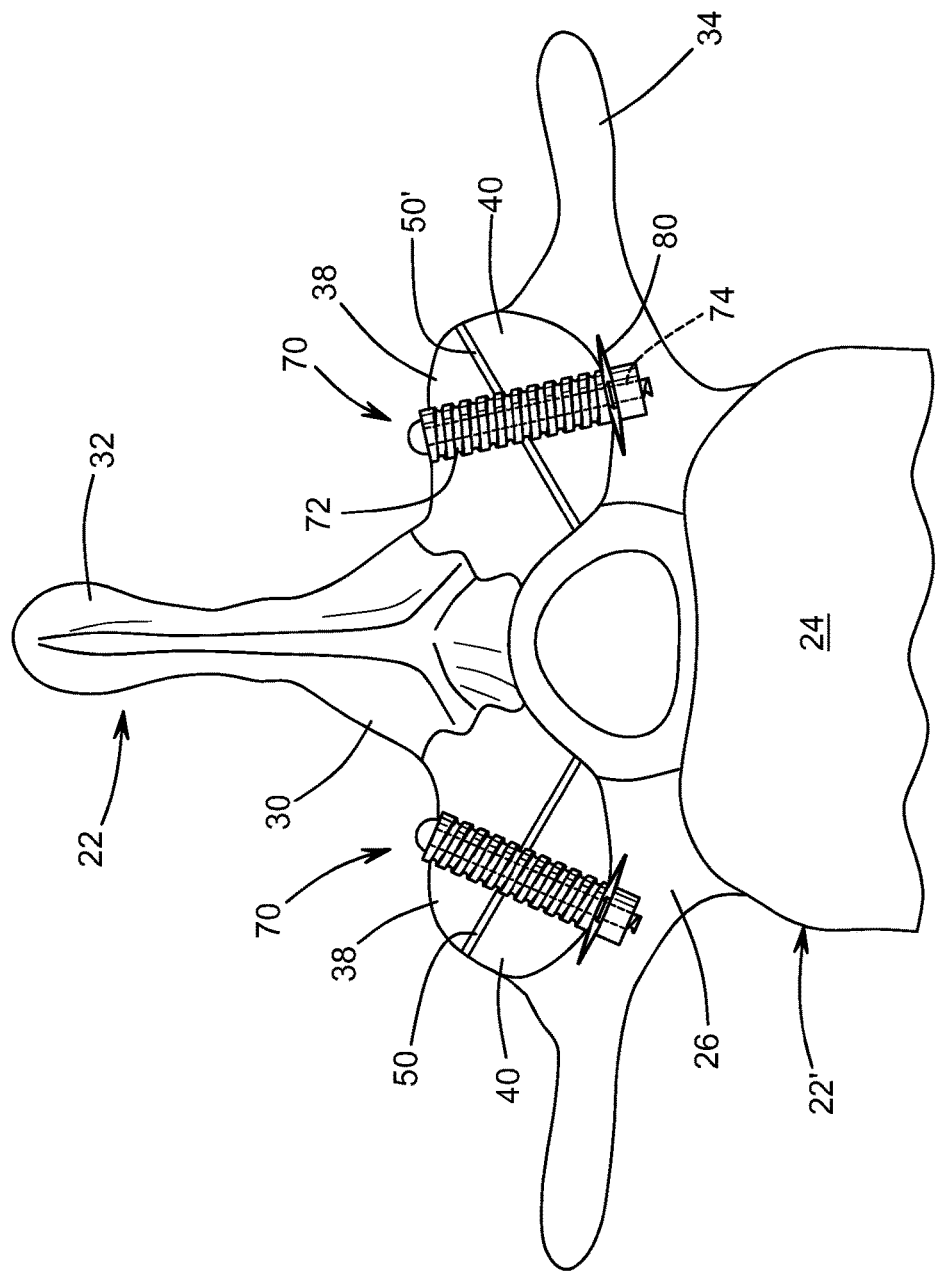
FIG. 1B illustrates a first exemplary manner in which a first embodiment of the fusion device of this invention can be installed on the two vertebrae illustrated in FIG. 1.
Figure 1C:
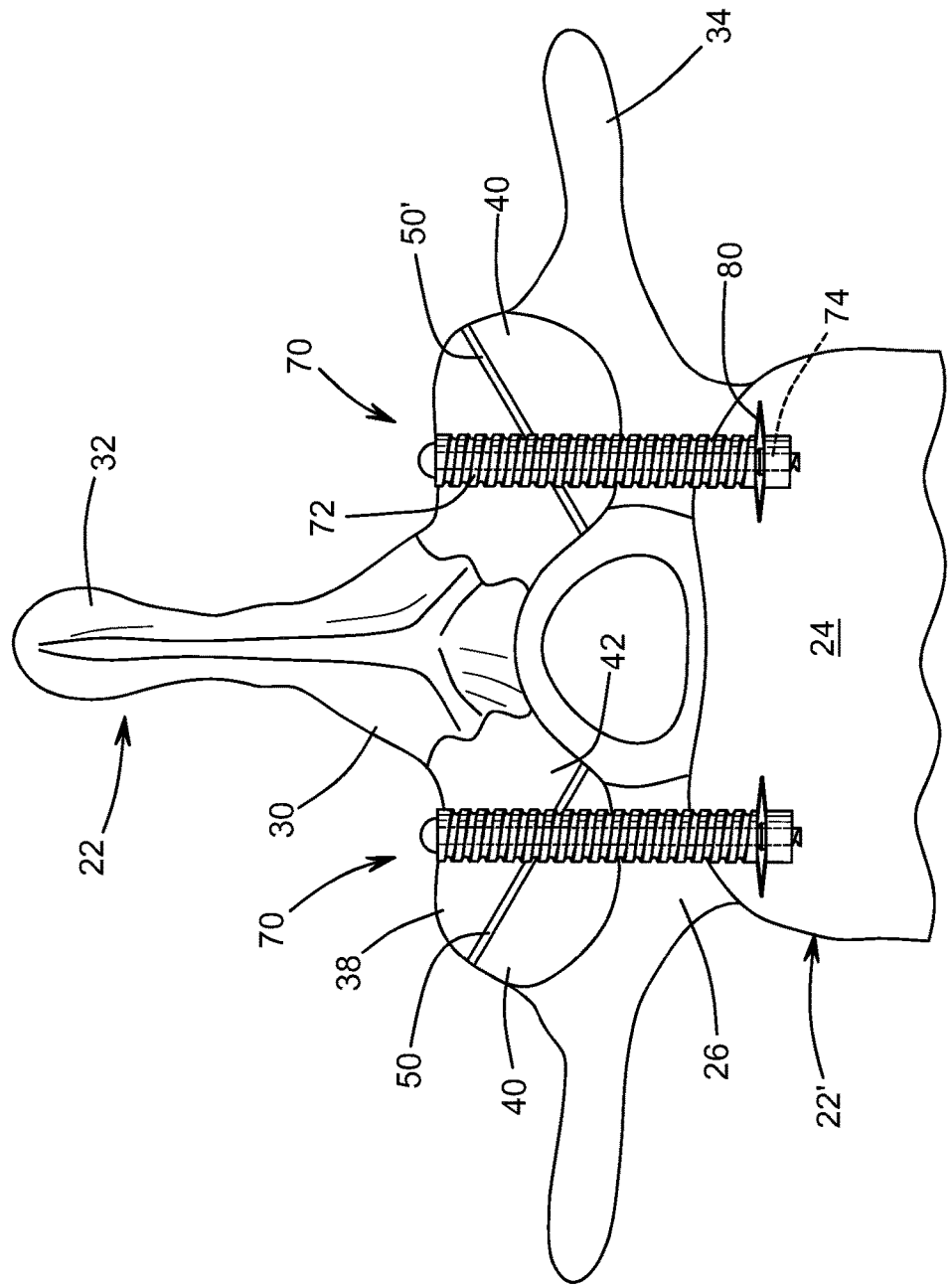
FIG. 1C illustrates a second exemplary manner in which the first embodiment of the fusion device of this invention can be installed on the two vertebrae illustrated in FIG. 1.
Figure 2:
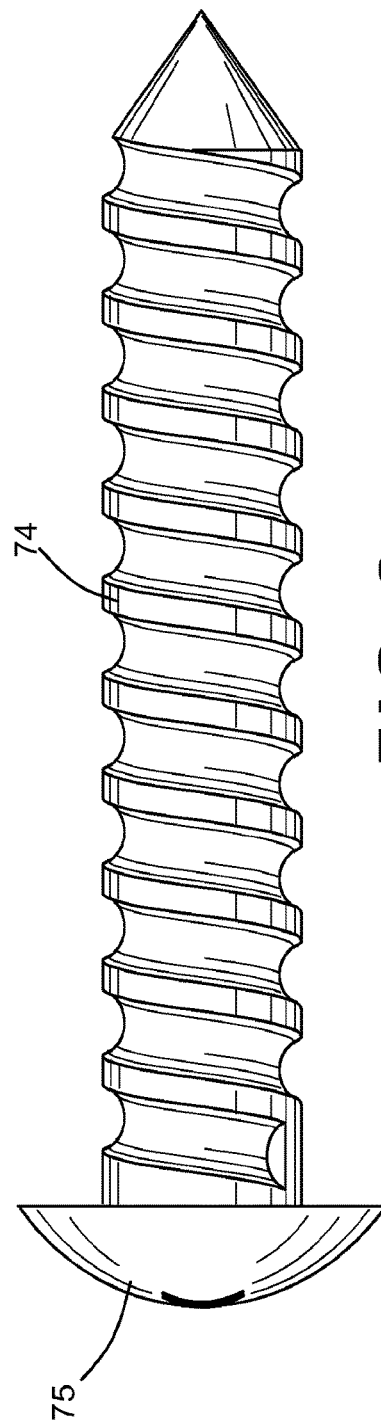
FIG. 2 is an enlarged elevational view of a first embodiment of a bone screw portion of the first embodiment of the fusion device.
Figure 3:
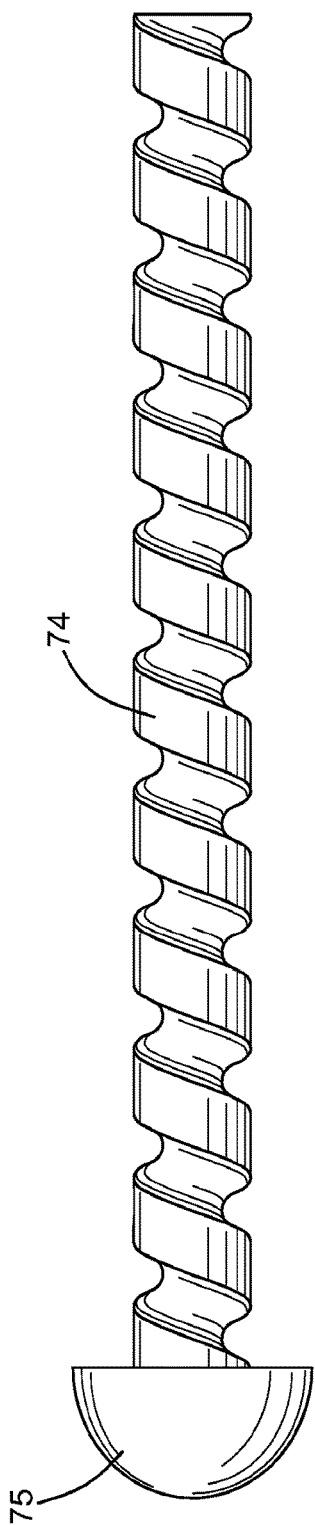
FIG. 3 is an enlarged elevational view of a second embodiment of a bone screw portion of the first embodiment of the fusion device.
Figure 4:
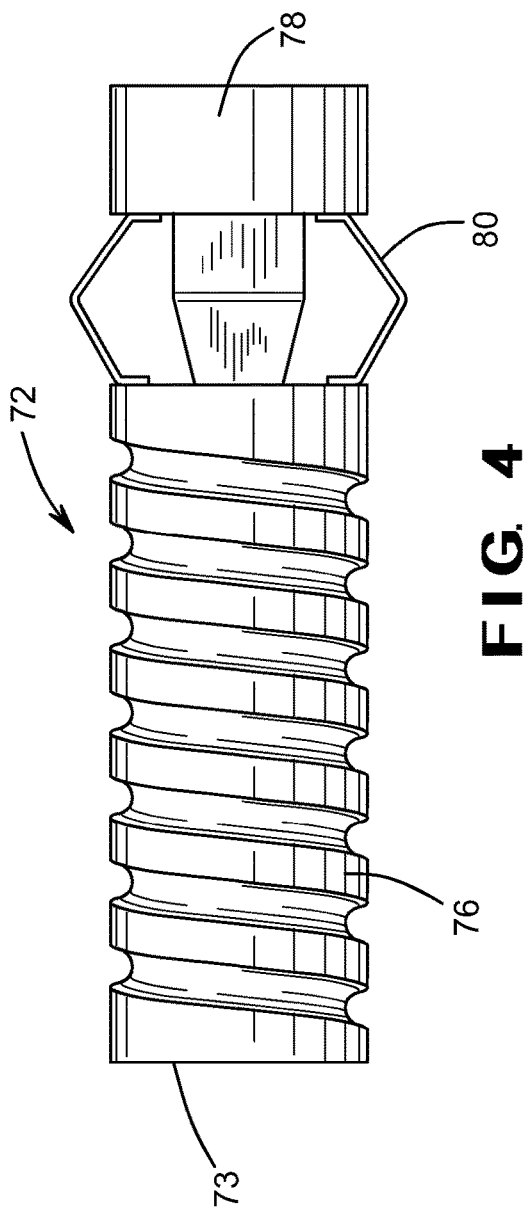
FIG. 4 is an enlarged elevational view of a bone dowel portion of the first embodiment of the fusion device.
Figure 5:
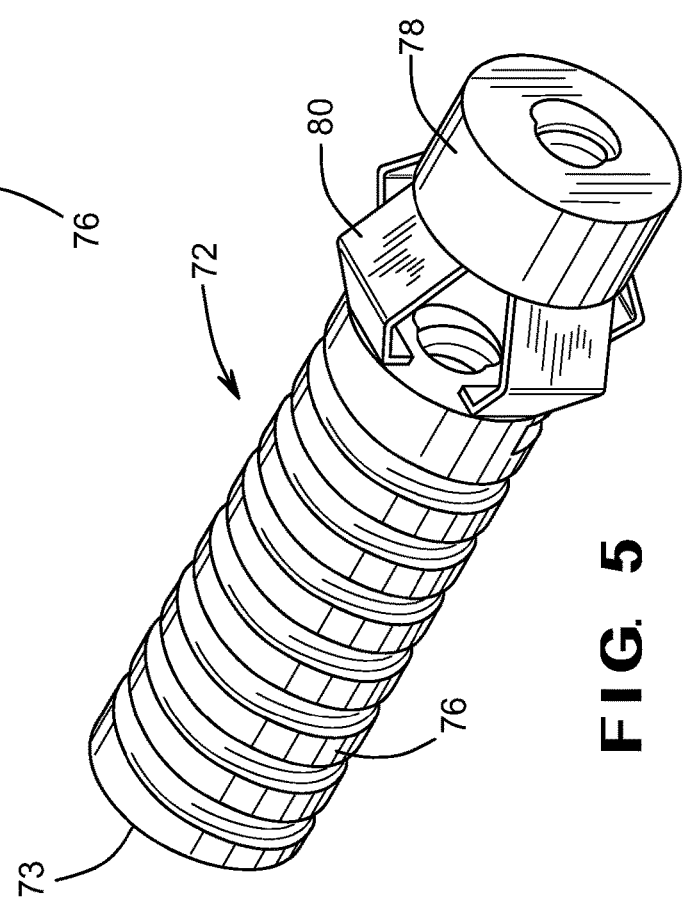
FIG. 5 is an enlarged perspective view of a bone dowel portion of the first embodiment of the fusion device illustrated in FIG. 4.

As shown in various embodiments in FIGS. 1A, 1B, and 1C, a first embodiment of a fusion device 70 includes a hollow bone dowel portion 72. The illustrated hollow bone dowel portion 72 is internally threaded for at least a distal portion of its length, although such is not required. A bone screw portion 74 of the fusion device 70 can be disposed within the hollow bone dowel portion 72. For example, the bone screw portion 74 of the fusion device 70 can be externally threaded and be threaded within the hollow bone dowel portion 72. The screw portion 74 of the fusion device 70 can be formed from any desired material including, for example, a metallic material such as titanium. As shown in FIG. 2, the screw portion 74 of the fusion device 70 can be formed from a solid body of material having an external helical thread or other similar structure provided thereon. Alternatively, as shown in FIG. 3, the screw portion 74 can be formed from a ribbon of material having a helical or other similar shape.

Figure 8:
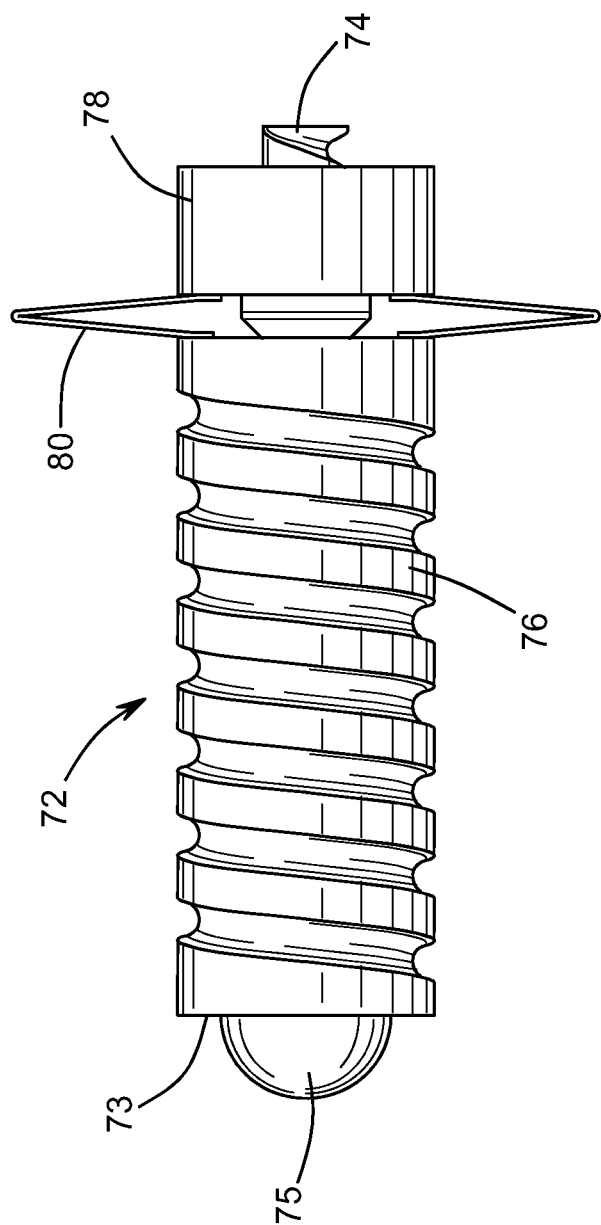
FIG. 8 is an enlarged elevational view of the second embodiment of the bone screw portion illustrated in FIG. 3 fully threaded within the bone dowel portion of the first embodiment of the fusion device.
Figure 9:
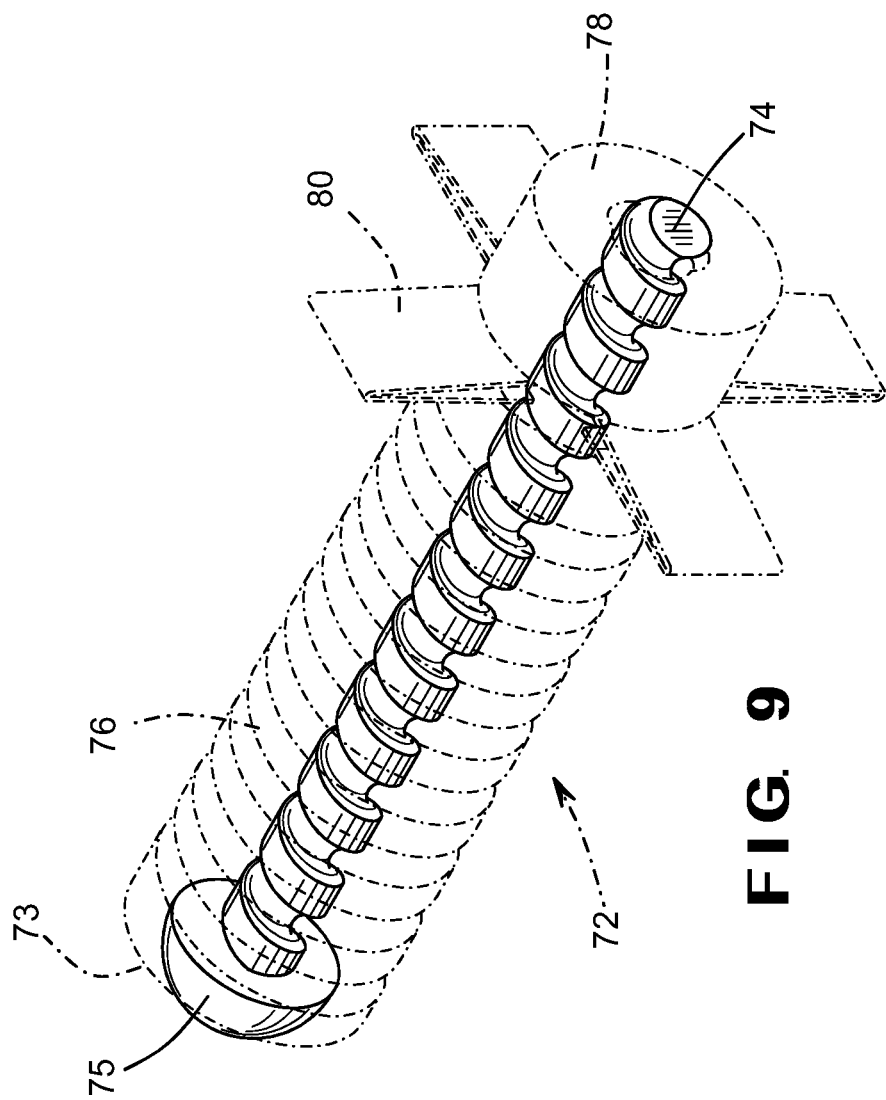
FIG. 9 is an enlarged perspective view, partially in phantom, of the second embodiment of the bone screw portion illustrated in FIG. 3 fully threaded with the bone dowel portion of the first embodiment of the fusion device.
Figure 10:
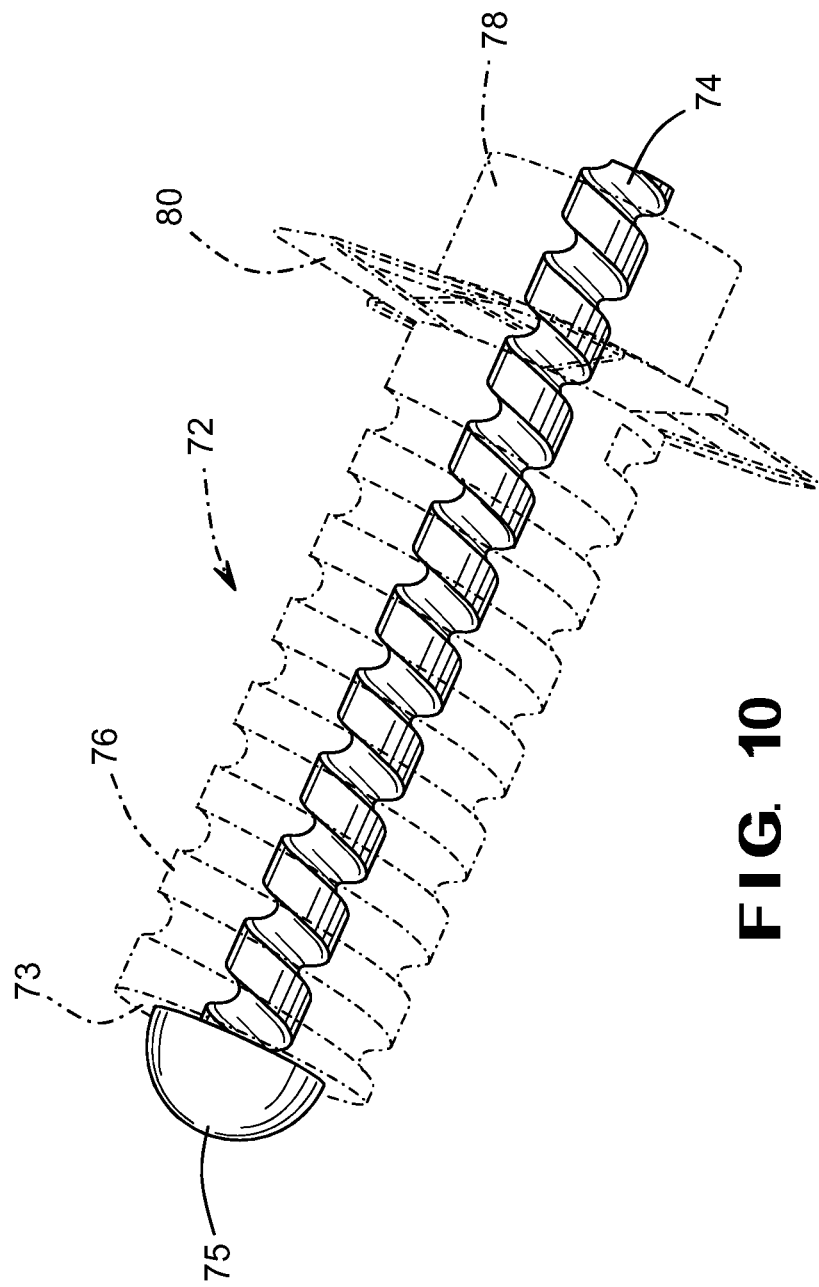
FIG. 10 is another enlarged perspective view, partially in phantom, of the second embodiment of the bone screw portion illustrated in FIG. 3 fully threaded with the bone dowel portion of the first embodiment of the fusion device.

The bone dowel portion 72 of the fusion device 70 can be formed from a bone-like or allograft composition and may include one or more external threads 76 for insuring insertion and resisting backwards slipping in or relative to the vertebrae 22 and 22'. Alternatively, the bone dowel portion 72 of the fusion device 70 may include one or more other structures, such as, for example, barbs, teeth, ribs and the like, for this purpose. At a distal end 78 of the dowel 72, a flexible flange 80 may be provided to aid in seating and/or compression relative to the vertebrae 22 and 22'. The distal end 78 of the dowel 72 may be internally threaded so as to cooperate with the externally threaded screw portion 74 for a purpose that will be explained below. Some or all of the bone dowel portion 72 of the fusion device 70 (including the flange 80) may be made of a flexible biocompatible polymer, such as polyaryletherketone ("PAEK"), polyetherketone ("PEEK") or UHMWPE or antioxidant stabilized UHMWPE. Such devices are sometimes referred to as PEEK constructs. When the screw 74 is threaded completely into the bone dowel 72, the screw head 75 seats against the proximal end 73 of the bone dowel 72. Continued turning of the screw 74 pulls the internally threaded distal portion 78 of the bone dowel 72 in a proximal direction and flattens the flanges 80 radially outwardly from a relaxed orientation (shown in FIGS. 4 through 7) to a compressed orientation (shown in FIGS. 8 through 10). Such deployment of the flanges 80 facilitates the installation of the fusion device 70 relative to the vertebrae 22 and 22', as shown in FIGS. 2 and 3.

The bone dowel portion 72 of the fusion device 70 can have any desired shape or size. In one embodiment, the diameter of the bone dowel 72 can range from about 3 mm to about 7 mm. In another embodiment, the diameter of the bone dowel 72 can range from about 4 mm to about 6 mm. Similarly, the length of the bone dowel 72 can range from about 16 mm to about 26 mm, or from about 20 mm to about 24 mm. The distal portion 78 of the bone dowel 72, including the uncompressed flange 80, can range from about 4 mm to about 8 mm long. The screw portion 74 can have a shaft of about 2 mm in diameter and, in certain preferred embodiments, is sufficiently long to engage the threaded distal portion of the bone dowel 72.

FIGS. 1A, 1B, and 1C show how the fusion device 70 can be positioned relative to the vertebrae 22 and 22'. Each of the vertebrae 22 and 22' includes laminae 30 that extend between a spinous process 32 and respective transverse processes 34. As shown in FIG. 1B, the fusion device 70 may be inserted through an inferior articular process 38 of the upper vertebra 22, across a facet joint gap 50, 50' between the vertebrae 22 and 22', and into a superior articular process 36 of the lower vertebra 22'. The fusion device 70 may optionally extending into a pedicle 26 of one of the vertebrae 22 and 22'.

Alternatively, as shown in FIG. 1C, the fusion device 70 may be inserted through the inferior articular process 38 of the upper vertebra 22, across the facet joint gap 50, 50' between the vertebrae 22 and 22', and into the superior articular process 40 of the lower vertebra 22'. However, in FIG. 1C, the fusion device 70 extends through a pedicle 26 and into the vertebral body 24 of the vertebra 22. As compared with the approach of FIG. 1B, the angle of insertion in FIG. 1C is more aligned anterior-posterior, and the angle of insertion the fusion device 70 forms with respect to the facet faces 41, 42 is more oblique. FIG. 1A shows how the fusion device 70 transects the surfaces 41, 42 of the facets, rather than being in the interfacet space between the vertebrae 22 and 22'.

During the installation of the fusion device 70, the surgeon only needs a minimal incision, for example, a very small standard midline approach, allowing the surgeon to work in his/her "comfort zone" for the midline partial laminectomy. In such a manner, the pars of the vertebra are preserved and up to 60% of the inferior facet is preserved, thus allowing for a fusion and stabilization across the facet joint. The fusion device 70 is placed in a minimally invasive procedure, thus minimizing the need for muscle retraction or dissection, often required to place "pedicle-based" stabilization systems.

Once surgically inserted, the closer the facet fusion device is located to the Center of Rotation (COR), the smaller and yet stronger the actual fixation of the device is within the vertebra. There is no "rod" per se like the pedicle screw/rod constructs. In this embodiment, the facet fusion device 70 harnesses the most "physiologic rod" of all, the bone across the facet joint 50, 50' and the pars areas above and below the facets. This "living, dynamic rod" allows for some flex without detrimental loosening of the facet fusion device. There is more "motion" than a rigid screw/rod construct, but there is also a solid locking implant and fusion across the facet joints (the only true joint in the spine), thus preventing further slippage, facet joint pain, etc. Additional levels of decompression are all linked together through this "living bone rod construct."

For an even more rigid construct in patients with greater instability, degenerative disc disease, etc. an interbody cage may optionally be added to the surgery, still preserving the lamina and facet construct. Alternatively, an interspinous fusion can be done with facet screws for further rotational stability.

The fusion device 70 described herein can provide the stability and, at the same time, deliver the bone graft material of the bone dowel portion 72 around the screw 74 directly at the fusion site. Thus, the fusion device 70 delivers bone graft material (when required) by bridging technology without an additional procedure and without compromising the stability of the fixation. As well as reducing the time required to perform surgery, the use of this fusion device 70 allows the surgeon to operate via a smaller incision. Both factors may contribute to a shorter recovery time for the patient. This fusion device 70 also reduces the likelihood of pseudoarthrosis.

FIGS. 11 through 13 illustrate a second embodiment of a fusion device, indicated generally at 100, in accordance with this invention. As shown therein, the fusion device 100 includes a screw portion 101 having a first externally threaded portion 102 and a second externally threaded portion 103. The screw portion 101 may be formed from any desired material, including that described above in connection with the bone screw 74. The fusion device 100 also includes a hollow bone dowel portion 104 that, when assembled, extends about the screw portion 101. The bone dowel portion 104 may include an internally threaded portion (not shown) that engages the second externally threaded portion 103 of the screw portion 101, although such is not required. The fusion device 100 further includes a head portion 105 having an internally threaded portion (not shown) that engages the second externally threaded portion 103 of the screw portion 101. As a result, the hollow bone dowel portion 104 is retained about the screw portion 101 between the head portion 105 and the first externally threaded portion 102, as best shown in FIGS. 11 and 12. The fusion device 100 can be sized and shape as desired to deliver the bone graft material of the bone dowel portion 104 directly at the fusion site in the manner described above.

Figure 14:
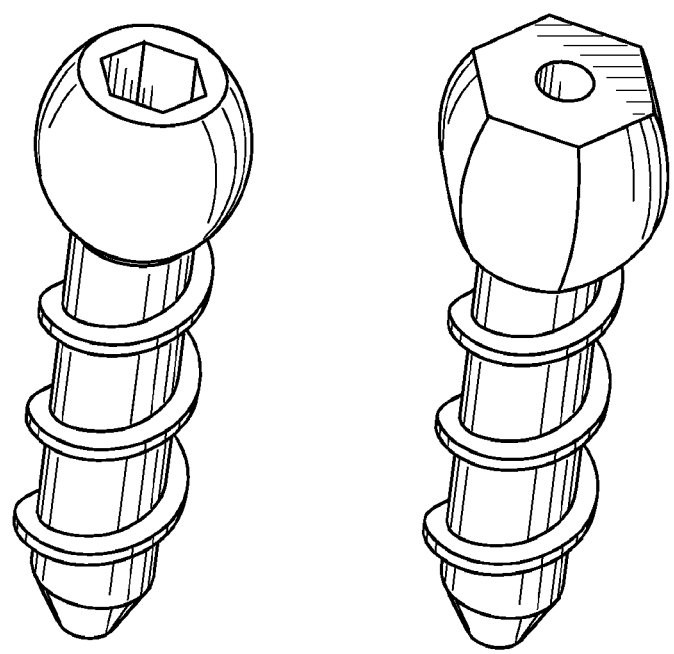
FIG. 14 is a perspective view of a full bone screw and bone screw and internal metal screw.

FIG. 14 is a perspective view of a full bone screw and bone screw and internal metal screw.

Figure 15:
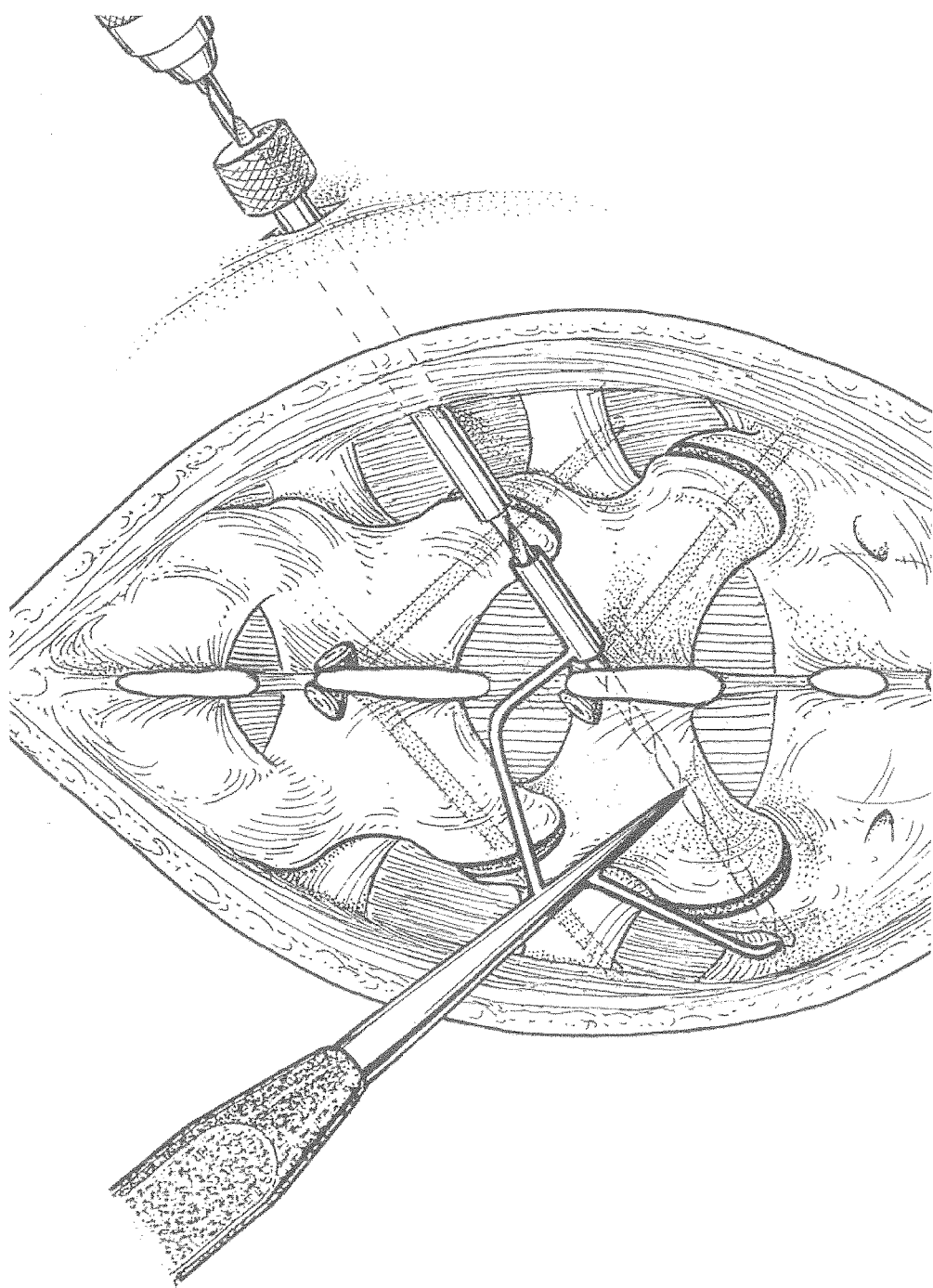
FIG. 15 illustrates how the fusion device of this invention passes through the lamina of the spine and then through the facet joint.

FIG. 15 illustrates how the fusion device of this invention passes through the lamina of the spine and then through the facet joint.

Other Embodiments

Hybrid Cage

The fusion device of this invention can be used in conjunction with an inter-body cage or/and interspinous fusion device. In one non-limiting example, a hybrid cage can be used as a non fusion device (disc-like action) or used as inter body fusion device in conjunction with proposed facet screws.

Dynamic Interspinous Device

In the last several years, the interspinous fusion procedure in patients above 65 is becoming a standard practice. In one non-limiting example, a dynamic interspinous device can be used in conjunction with a bone screw of the fusion device of this invention to increase its stability.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A fusion device comprising:
    a screw having a head and a shaft, wherein the screw is formed from a solid body of material having an external helical thread or other similar structure provided thereon; and
    a hollow dowel disposed about the shaft of the screw, wherein the dowel is composed of a material selected from the group consisting of a bone-like material, a biocompatible material, a biocompatible polymer, an allograft material, and combinations thereof;
    wherein the shaft has an externally threaded portion, the dowel has a proximal end located adjacent to the head of the screw and a distal end, and the distal end of the dowel has an internally threaded portion that cooperates with the externally threaded portion of the shaft;
    wherein the dowel has a flange provided between the proximal end and the distal end; and
    wherein the flange is radially outwardly moveable from a relaxed orientation to a compressed orientation in response to rotation of the screw relative to the flange, wherein the compressed orientation flattens the flange.

2. The fusion device defined in claim 1 wherein the dowel is retained on the shaft between the head of the screw and the externally threaded portion.

3. The fusion device defined in claim 1 wherein the screw is formed from a ribbon of material having a helical or other similar shape.

4. The fusion device defined in claim 1 wherein the biocompatible polymer is selected from the group consisting of a polyaryletherketone (PAEK), a polyetherketone (PEK), a polyetheretherketone (PEEK), a polyetherketoneketone (PEKK), a polyetheretherketoneketone (PEEKK), a polyetherketoneetherketoneketone (PEKEKK), an ultra-high molecular weight polyethylene (UHMWPE), an anti-oxidant stabilized UHMWPE, and combinations thereof.

5. The fusion device defined in claim 1 wherein the dowel includes one or more external threads, external barbs, external teeth, and/or external ribs.

6. The fusion device defined in claim 1 wherein the screw is formed from a metallic material.

7. A method of fixation and/or fusion of a facet joint of adjacent vertebrae comprising the steps of:
    (a) providing a fusion device as defined in claim 1; and
    (b) inserting the fusion device through an inferior articular process of a first vertebra, transversely across the facet joint, and into a superior articular process of a second vertebra that is adjacent to the first vertebra.

8. A method of stabilizing a spine and/or avoiding slippage between adjacent vertebrae comprising the steps of:
    (a) providing a fusion device as defined in claim 1; and
    (b) inserting the fusion device through an inferior articular process of a first vertebra, transversely across the facet joint, and into a superior articular process of a second vertebra that is adjacent to the first vertebra.

9. A method of treating spinal stenosis, lumbar spinal stenosis, cervical spinal stenosis, a facet joint condition, a facet joint disease, facet syndrome, spinal osteoarthritis, spondylosis, spinal spondylosis, and/or cervical spondylosis comprising the steps of:
    (a) providing a fusion device as defined in claim 1; and
    (b) inserting the fusion device through an inferior articular process of a first vertebra, transversely across the facet joint, and into a superior articular process of a second vertebra that is adjacent to the first vertebra.

10. A hybrid device comprising:
    a prosthetic intervertebral disc or an interspinous fusion device; and
    a fusion device as defined in claim 1 coupled or uncoupled to the prosthetic intervertebral disc or the interspinous fusion device.

11. The hybrid device defined in claim 10 wherein the fusion device is coupled to the prosthetic intervertebral disc or the interspinous fusion device.

12. The hybrid device defined in claim 10 wherein the fusion device is uncoupled to the prosthetic intervertebral disc or the interspinous fusion device.

13. The fusion device of claim 1, wherein the screw is non-hollow.

* * * * *